United States Patent
Kimoto et al.

(10) Patent No.: US 9,454,830 B2
(45) Date of Patent: Sep. 27, 2016

(54) MEDICAL IMAGE-PROCESSING APPARATUS, X-RAY CT APPARATUS, AND A MEDICAL IMAGE-PROCESSING METHOD

(71) Applicant: Toshiba Medical Systems Corporation, Otawara-shi (JP)

(72) Inventors: Tatsuya Kimoto, Otawara (JP); Yasuko Fujisawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/122,557

(22) PCT Filed: Feb. 1, 2013

(86) PCT No.: PCT/JP2013/052332
§ 371 (c)(1),
(2) Date: Nov. 26, 2013

(87) PCT Pub. No.: WO2013/115354
PCT Pub. Date: Aug. 8, 2013

(65) Prior Publication Data
US 2014/0099013 A1 Apr. 10, 2014

(30) Foreign Application Priority Data
Feb. 2, 2012 (JP) ................................ 2012-020441

(51) Int. Cl.
| | |
|---|---|
| *G06K 9/00* | (2006.01) |
| *G06T 11/00* | (2006.01) |
| *A61B 6/03* | (2006.01) |
| *A61B 6/00* | (2006.01) |
| *G06T 7/00* | (2006.01) |

(52) U.S. Cl.
CPC ............ *G06T 11/005* (2013.01); *A61B 6/032* (2013.01); *A61B 6/5264* (2013.01); *G06T 7/0012* (2013.01); *A61B 2576/023* (2013.01)

(58) Field of Classification Search
None
See application file for complete search history.

(56) References Cited

U.S. PATENT DOCUMENTS

| | | | |
|---|---|---|---|
| 2009/0161818 A1 | 6/2009 | Sakurai et al. | |
| 2010/0202675 A1 | 8/2010 | Takanaka et al. | |
| 2013/0004044 A1* | 1/2013 | Ross et al. | 382/131 |
| 2013/0194266 A1* | 8/2013 | Forster | 345/424 |
| 2013/0237804 A1* | 9/2013 | Brown et al. | 600/410 |

FOREIGN PATENT DOCUMENTS

| | | |
|---|---|---|
| JP | 2002-360563 | 12/2002 |
| JP | 2009-183468 | 8/2009 |
| JP | 2010-201157 | 9/2010 |

OTHER PUBLICATIONS

Gorbunova, "Image registration of lung CT scans for monitoring disease progression", Copenhagen 2010.*
Sarrut, et al., "Simulation of four-dimensional CT images from deformable registration between inhale and exhale breath-hold CT scans", Medical Physics, vol. 33, Issue 3, Mar. 2006, pp. 605-617.
International Search Report issued Mar. 26, 2013, in PCT/JP13/052332 filed Feb. 1, 2013.
Vladlena Gorbunova et al. "Mass Preserving Image Registration for Lung CT", Medical Image Analysis 16 (2012), pp. 786-795 (10 pages).
Office Action mailed Mar. 7, 2016 in Chinese Patent Application No. 201380002581.6.

\* cited by examiner

*Primary Examiner* — Soo Park
(74) *Attorney, Agent, or Firm* — Oblon, McClelland, Maier & Neustadt, L.L.P.

(57) ABSTRACT

A medical image-processing apparatus that corrects divergence, even in a case where divergence in CT numbers occurs throughout a plurality of sets of image data that have been acquired for anatomically identical areas because the observed object is undergoing shape-alteration. The apparatus includes an image data storage, an extractor, and a corrector. The image data storage stores respective sets of image data acquired by scanning a targeted region undergoing chronological shape-alteration in a subject, the scanning having been executed at predetermined respective timings. The extractor extracts image data that correspond to the targeted region out of each of the respective sets of image data. The corrector calculates degrees of shape-alteration of the targeted region in the respective extracted sets of images data and to correct CT numbers of the respective sets of image data extracted for the targeted region, based on calculated degrees.

7 Claims, 6 Drawing Sheets

FIG. 5

MEDICAL IMAGE-PROCESSING APPARATUS, X-RAY CT APPARATUS, AND A MEDICAL IMAGE-PROCESSING METHOD

TECHNICAL FIELD

Embodiments according to the present invention relate to technologies used for a medical image-processing apparatus, an X-ray CT apparatus and a medical image-processing method.

BACKGROUND ART

There is a medical image-processing apparatus for displaying three-dimensional image data that have been acquired by a diagnostic medical imaging apparatus. The diagnostic medical imaging apparatus herein includes an X-ray Computed Tomography (CT) apparatus, an Magnetic Resonance Imaging (MRI) apparatus, an X-ray diagnosis apparatus, an ultrasound diagnosis apparatus, etc. The medical image-processing apparatus is an apparatus that executes image-processing on image data that have been generated by the diagnostic medical imaging apparatus.

In addition, the diagnostic medical imaging apparatus includes an apparatus that enables scanning sessions per a unit of time for a relatively wide region in high-definition (high-resolution) images as does a multi-slice X-ray CT apparatus, which comprises a 2D detector. The 2D detector has a plurality of detector elements, which are arranged in an array of rows and columns, with the total number of elements being defined by "m" channels times "n" columns (the "m" and "n" are positive integers). While one row of detector elements are used in a single-slice X-ray CT apparatus, the 2D detector has rows in a plurality of columns (for example, four columns, eight columns, etc.) in the direction perpendicular to the rows.

The larger the detector (i.e., the greater the number of detector elements) employed in the multi-slice X-ray CT apparatus, the wider the region covered by the projection data acquired by a session of scanning. In other words, the multi-slice X-ray CT apparatus equipped with such a detector is effective in chronologically scanning a predetermined region for acquisition of volume data, which can be generated at a high frame-rate. This type of scanning, which is hereinafter referred to as "Dynamic Volume scan", provides three-dimensional images and enables the operator to evaluate the motion per a unit of time of the scanned region.

In addition, the medical image-processing apparatus generates medical images based on image data acquired with such diagnostic medical imaging apparatus. The medical image-processing apparatus generates medical images, for example, based on volume data that have been reconstructed by an X-ray CT apparatus.

PRIOR ART REFERENCES

Patent Reference

[Patent Reference 1] Japanese Laid-Open Patent Publication No. 2010-201157

SUMMARY OF THE INVENTION

Problems to be Solved by the Invention

On the one hand, some types of image-processing are performed on CT numbers, and on the other hand, CT numbers are used also for analysis. For example, in image data that have been acquired by scanning a lung as object to be observed, CT numbers for the part affected by pulmonary emphysema (affected part) are different from CT numbers for the other part. Accordingly, CT numbers in image data are analyzed with a medical image-processing apparatus, so as to specify areas that indicate pulmonary emphysema. When positional matching is executed among a plurality of sets of image data acquired at different timings, CT numbers in image data are used for specifying anatomically identical areas so as to improve precision of image-aligning. By the way, the term "anatomically identical areas" means, for example, that they match one another in composition.

However, organs like the lungs or the heart undergo expansion and contraction, or shape-alteration over a period of time. Consequently, at different timings, the tissues forming such organs show changes in density or density distribution (both these terms are hereinafter represented by "density"). Because of the changes in density, CT numbers for anatomically identical areas may differ in a plurality of sets of image data that have been acquired at different timings if such a shape-altering region is set as object to be observed. If the CT numbers are assigned different for the same area, then there may be a case where the above-described analytical processing or positional matching cannot be executed correctly.

Embodiments according to the present invention are to provide medical image-processing apparatus that can correct such divergence as mentioned above, even in a case where divergence in CT numbers occurs throughout a plurality of sets of image data that have been acquired for anatomically identical areas because the observed object is undergoing shape-alteration.

Means for Solving the Problems

A first aspect of this embodiment is a medical image-processing apparatus comprising: an image data storage unit, an extraction unit and a correction unit. The image data storage unit is configured to store respective sets of image data that have been acquired by scanning a targeted region undergoing chronological shape-alteration in a subject, the scanning having been executed at predetermined respective timings. The extraction unit is configured to extract image data that correspond to the targeted region out of each of the respective sets of image data. The correction unit is configured to calculate degrees of shape-alteration of the targeted region in the respective extracted sets of images data and to correct CT numbers of the respective sets of image data that have been extracted for the targeted region, based on the calculated degrees.

A second aspect of this embodiment is an X-ray CT apparatus comprising: a scanning unit, an extraction unit and a correction unit. The scanning unit is configured to acquire a plurality of sets of image data by scanning a targeted region undergoing chronological shape-alteration in a subject, the scanning being executed at predetermined respective timings. The extraction unit is configured to extract image data that correspond to the targeted region out of each of the respective sets of image data. The correction unit is configured to calculate degrees of shape-alteration of the targeted region in the respective extracted sets of image data and to correct CT numbers of the respective sets of image data that have been extracted for the targeted region based on the calculated degrees.

PREFERRED EMBODIMENTS OF THE INVENTION

First Embodiment

Figure 1:
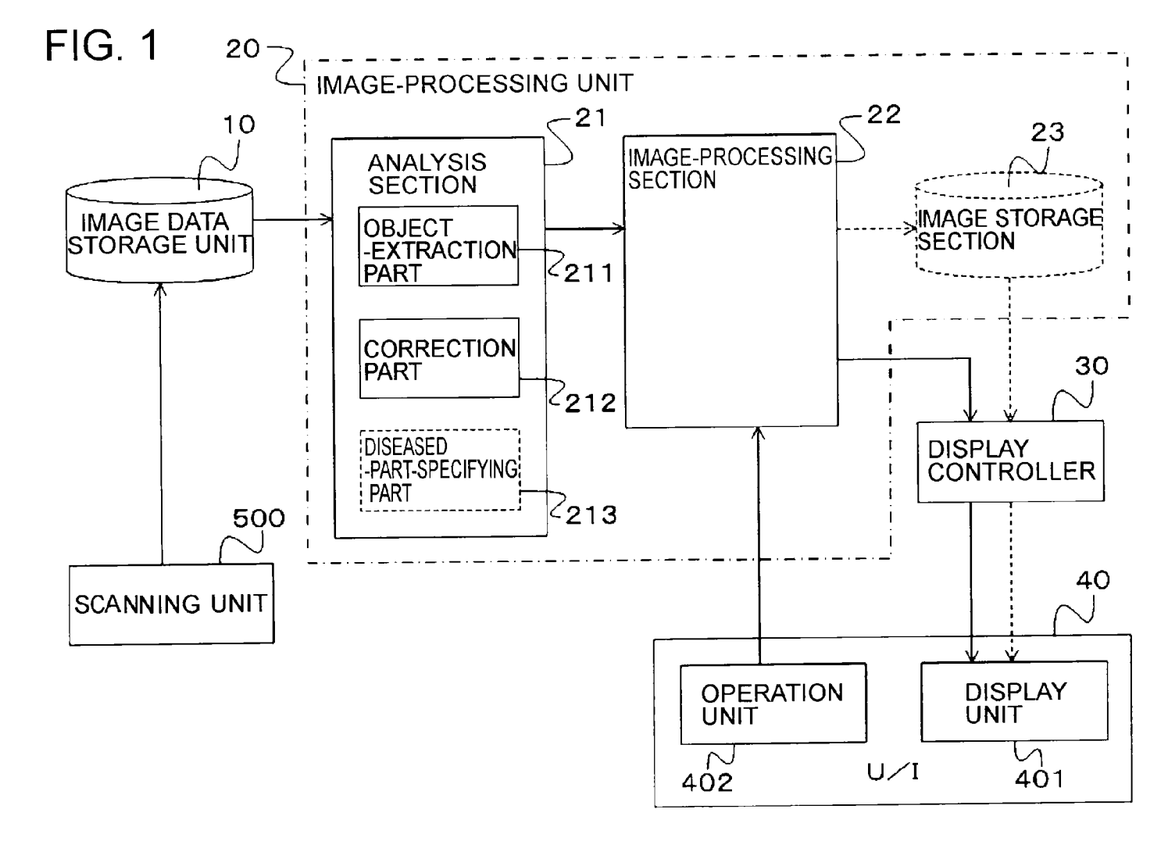
FIG. 1 is a block diagram showing the configuration of medical image-processing apparatus as an embodiment.

Medical image-processing apparatus as a first embodiment generates medical images based on image data (e.g., volume data) acquired with diagnostic medical imaging apparatus, for example, an X-ray CT apparatus. Hereinafter, the configuration of the medical image-processing apparatus as this embodiment is described with reference to FIG. 1. As shown in FIG. 1, a medical image display apparatus according to this embodiment is configured to include an image data storage unit 10, an image-processing unit 20, a display controller 30, and a U/I 40. Here, the U/I 40 is a user interface, which is configured to include a display unit 401 and an operation unit 402.

(Image Data Storage Unit 10)

The image data storage unit 10 is a storage unit, which stores three-dimensional image data (for example, volume data) that are acquired with a scanning unit 500 by scanning a subject at a plurality of timings per examination. The scanning unit 500 is a diagnostic medical imaging apparatus, for example, an X-ray CT apparatus that can acquire three-dimensional image data. Hereinafter, such three-dimensional image data are referred to as "image data". In the following descriptions, the term "image data" represent volume data acquired by an X-ray CT apparatus.

(Image-Processing Unit 20)

The image-processing unit 20 is configured to include an analysis section 21, an image-processing section 22, and an image storage section 23.

(Analysis Section 21)

The analysis section 21 is configured to include an object-extraction part 211 and a correction part 212. The analysis section 21, at first, reads out a plurality of sets of image data, which have been acquired by scanning the subject at different timings, from the image data storage unit 10, by reading set by set of image data from the plurality of sets of image data, which have been acquired at the respective timings. The analysis section 21 outputs the respective sets of image data, which have been read out, to the object-extraction part 211. The data output by the analysis section 21 also functions as an instruction for extraction of objects.

(Object-Extraction Part 211)

The object-extraction part 211, after having received image data for each of the respective timings, extracts objects, which correspond to organs such as the lungs and the heart, from the respective sets of medical image data, based on voxel values in each set of medical image data. The object-extraction part 211, after having extracted an object in each region, executes processing that is based on biological information, for example, segmentation processing. By doing so, the object-extraction part 211 specifies, as object to be analyzed, an object that corresponds to a region (for example, a lung) substantially identical throughout the respective sets of images, which have been scanned at different timings. By the way, this specification is executed respectively on every set of image data acquired at a different timing. The object-extraction part 211 makes each piece of information indicating the object that has been specified for a corresponding timing, accompany the image data from which the information has been extracted, and the object-extraction part 211 outputs the image data to the correction part 212.

(Correction Part 212)

Figure 2A:
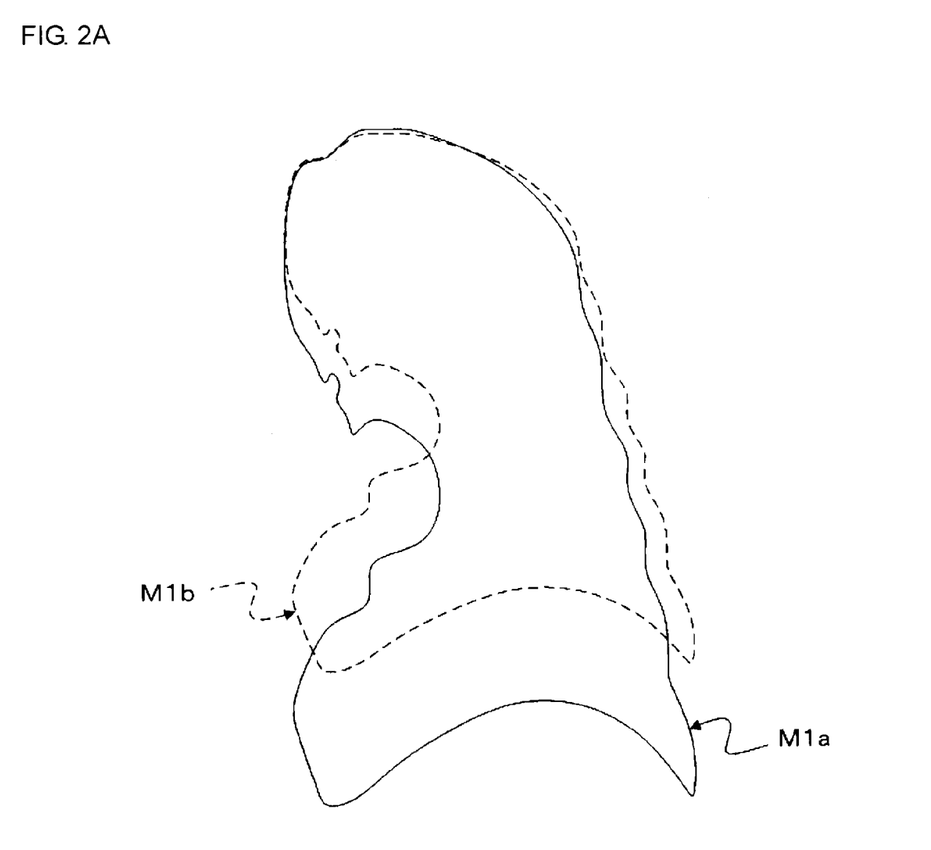
FIG. 2A is a drawing for describing density changes due to shape-alteration or contraction of an observed object.
Figure 2B:
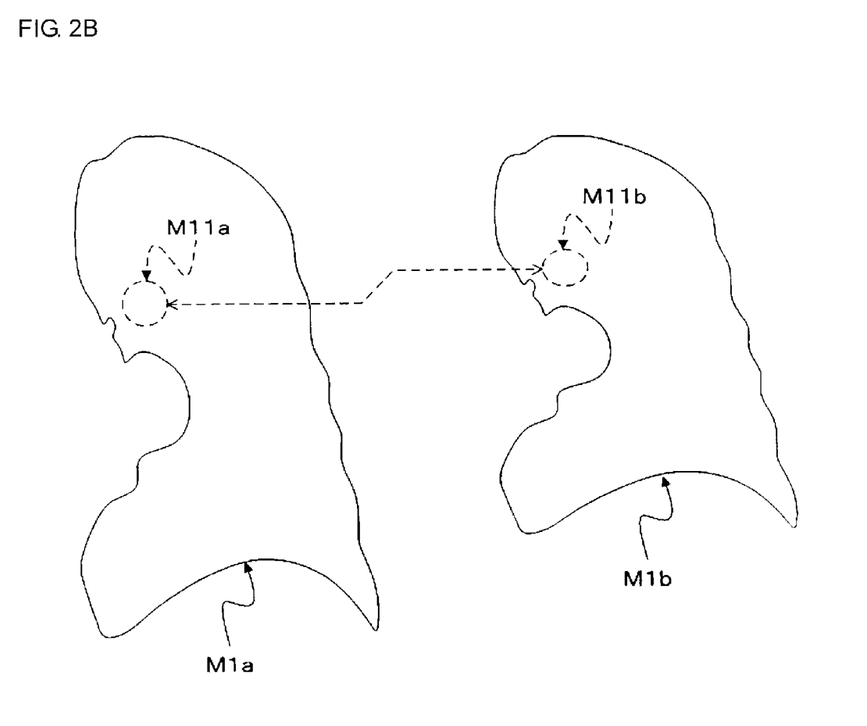
FIG. 2B is a drawing for describing density changes due to shape-alteration or contraction of an observed object.

Now, reference is made to FIG. 2A and FIG. 2B. FIGS. 2A and 2B are drawings for describing density changes caused by the shape-alteration or contraction of an observed object. Reference numeral "M1a" in FIGS. 2A and 2B schematically shows an outline of a lung in expansion. On the other hand, "M1b" shows an outline of the same lung in contraction at a timing that is different from that of "M1a". In the following description, if timings are not mentioned specifically, then "M1" may be used instead of "M1a" and "M1b". In addition, areas M11a and M11b shown in FIG. 2B indicate, respectively, predetermined areas that anatomically correspond each other (i.e., their composition is identical) between "M1a" and "M1b". In the following description, if timings are not mentioned specifically, then "area M11" is used instead of areas M11a and M11b.

As indicated by M1a and M1b, the lungs repeatedly undergo expansion and contraction in synchronization with respiration, and therefore, their density differs depending on the timing at which scanning is performed. Due to changes in density, sets of image data that have been acquired at different timings may indicate, respectively, different CT numbers for an anatomically identical area (for example, areas M11a and M11b). Consequently, differences in CT numbers, for example, for the areas M11a and M11b that are actually the same anatomically identical area, may lead to a determination that they are of different materials (i.e., different areas). If such a problem occurs in a case where the medical image-processing apparatus is utilized for specifying regions affected by such diseases as pulmonary emphysema and tumor on the basis of CT numbers, then diseased parts may not be detected correctly. In such a case, different CT numbers that are captured in the respective sets of image data for the same anatomically identical area lead to a determination that each is a different area. As a result, the medical image-processing apparatus cannot execute precise positional-matching on the respective sets of image data. To solve such problems, the correction part 212 corrects the divergence of CT numbers that has been caused by density changes. The following is a specific description of actions taken by the correction part 212.

The correction part 212 receives image data for each predetermined timing from the object-extraction part 211. The received image data are accompanied with information that indicates the object in the region being analyzed as mentioned above. The correction part 212 extracts information indicating the object from each set of image data.

The correction part 212 calculates the volume of the object based on the information indicating the object, which has been extracted. This object corresponds to, for example, the region being analyzed. Assuming that the mass of the extracted object is constant (for example, a sample value), the correction part 212 divides the mass by the volume. By doing so, the correction part 212 calculates the density of the object as a relative value. This calculated density is hereinafter referred to as "relative density". In this way, for each set of image data, the relative density of the object is calculated as analysis of the object included in the image data.

Figure 3:
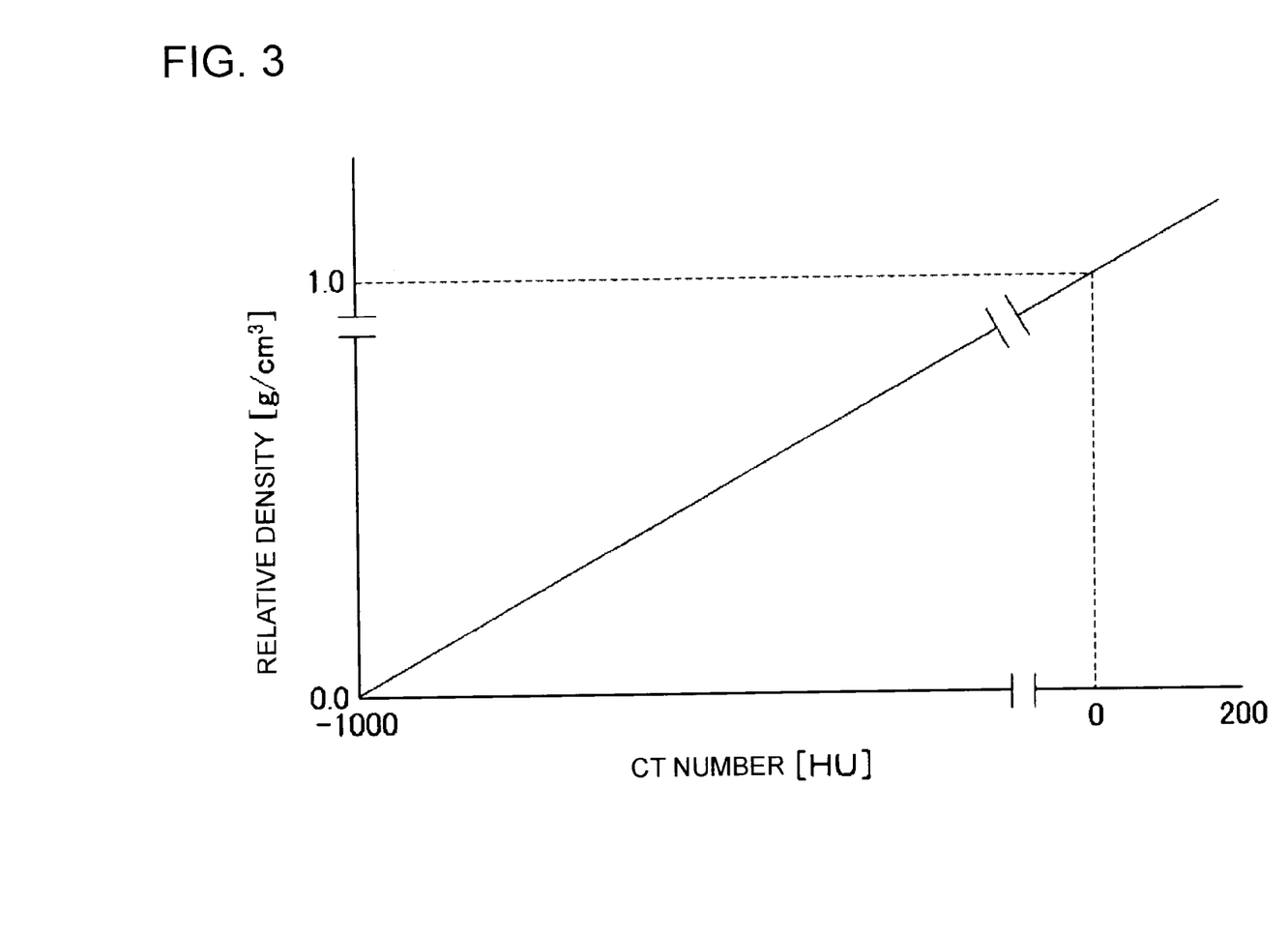
FIG. 3 is an example of management information that indicates changes in CT numbers in relation to changes in relative density.

Furthermore, the correction part 212 has, in memory beforehand, management information that indicates changes in CT numbers in relation to changes in relative density. FIG. 3 describes an example of such management information. In FIG. 3, while the vertical axis expresses relative densities, the horizontal axis expresses CT numbers. This management information has been prepared in advance, for example, on the basis of the result of an experiment conducted for measuring relations between relative densities and CT numbers. The management information prepared in such a way has been stored in the correction part 212.

The correction part 212 compares the relative density of the object calculated for each set of image data to the management information, which is shown in FIG. 3, and the correction part 212 specifies the divergence of CT numbers in relation to chronological density-changes of the region. Specifically, the correction part 212 calculates the difference between the relative density of the object that corresponds to a predetermined timing as a reference and the relative density of the object that corresponds to another timing. The correction part 212 specifies the divergence in CT numbers that corresponds to the difference between the relative densities, based on the management information. In the above-mentioned method, the relative density of the object that corresponds to a predetermined timing is used as a reference for specifying the divergence in CT numbers. The present embodiment is, however, not restricted to this. For example, a relative density as a predetermined sample value may be applied as reference for specifying the divergence in CT numbers.

Based on the information that indicates the specified divergence in CT numbers, the correction part 212 corrects CT numbers for the part that corresponds to the analyzed object in the image data. This correction is executed for the plurality of sets of image data, so that CT numbers for the anatomically identical area correspond one another throughout the plurality of sets of image data. In this way, if a divergence in CT numbers occurs between sets of image data because of density changes caused by chronological expansion and contraction or shape-alteration, the medical image-processing apparatus equipped with the above-described processing method is capable of identifying anatomically identical areas as areas having the same CT numbers (i.e., areas having the same composition).

In this way, the correction part 212 corrects CT numbers that experience relative changes with respect to the shape-alteration or contraction of an observed object, on the basis of any state of the object (as a predetermined relative density), so that CT numbers for an anatomically identical area are made to agree relatively throughout a plurality of sets of image data. There is, therefore, no need for the medical image-processing apparatus to determine the density in absolute value for specifying the divergence in CT numbers. By the way, if the mass of the region being analyzed can be calculated, then based on the mass and the volume of the object, the density may be calculated in absolute value instead of in relative density. Such densities in absolute value as well as relative densities are examples of "density information".

In the above-mentioned description, density changes caused by the shape-alteration or contraction of an observed object are described as equally changing throughout the observed object notwithstanding points therein. However, the application of the processing by the medical image-processing apparatus as this embodiment is not limited to this condition. For example, there are morphological features like nodes, whose degree of shape-alteration and contraction is smaller than others (i.e., the divergence in CT numbers is comparatively small). If errors of this degree are not tolerable, then the medical image-processing apparatus specifies the part whose degree of shape-alteration or expansion and contraction is comparatively small as mentioned above, for example, by shape analysis. Furthermore, the medical image-processing apparatus executes weighting on the amounts of relative density changes in other parts in accordance with positional relations (for example, distances) between the specified part and the other parts. After that, the medical image-processing apparatus specifies the divergence in CT numbers for each point, based on the above-described management information and the weights. In addition, as another method, the medical image-processing apparatus divides the observed object into a plurality of areas and generates management information for each area. In this method, furthermore, the medical image-processing apparatus corrects CT numbers for each area, based on the management information for each of the respective areas.

The correction part 212 outputs image data whose CT numbers have been corrected, to the image-processing section 22. In this way, for example, when positional matching is executed by specifying an anatomically identical position on a plurality of sets of image data that have been acquired at different timings, the image-processing section 22 can specify the anatomically identical area as the area with the same CT numbers. The medical image-processing apparatus can improve the precision of positional matching by applying positional matching in accordance with this method together with positional matching in accordance with another method (for example, positional matching based on morphological features). In addition, even in a case where medical images are generated to enable selective display of a desired object by executing threshold processing on CT numbers, since the divergence in CT numbers has been corrected, the image-processing section 22 can acquire similar processing results throughout the respective sets of image data.

(Diseased-Part-Specifying Part 213)

In addition, a diseased-part-specifying part 213 may be provided. The diseased-part-specifying part 213 specifies areas of diseased part affected by, for example, pulmonary emphysema or tumor, based on CT numbers in image data. In this case, the correction part 212 outputs image data whose CT numbers have been corrected to the diseased-part-specifying part 213. The diseased-part-specifying part 213 specifies diseased areas by analyzing the CT numbers in each set of image data. In other words, the diseased-part-specifying part 213 specifies, as diseased areas, such areas that indicate CT numbers that correspond to diseased part. For this purpose, CT numbers for areas with the same composition have been corrected so that the same CT numbers are assigned for such diseased areas in the respective sets of image data. Consequently, the diseased-part-specifying part 213 can readily specify diseased parts based on common CT numbers even in a case where the positions of diseased parts are different in different sets of image data. The diseased-part-specifying part 213 makes information that indicates specified diseased areas accompany the image data, and the diseased-part-specifying part 213 outputs the information together with the image data to the image-processing section 22. In this way, the image-processing section 22 can specify the diseased areas in medical images when the medical images are generated based on the image data, so as to generate identification information to make the diseased areas distinguishable in display.

(Image-Processing Section 22)

The image-processing section 22 receives, from the correction part 212 or the diseased-part-specifying part 213, the image data for respective timings whose CT numbers have been corrected. At this instant, the image-processing section 22 specifies anatomically identical areas scanned in the respective sets of image data, for example, based on the CT numbers of the respective sets of image data, and the image-processing section 22 may correlate them. In other words, the image-processing section 22 may use the corrected CT numbers of image data for improving the precision of positional matching performed on the respective sets of image data.

In addition, the image-processing section 22 may perform threshold processing on the image data with their CT numbers. By performing such threshold processing, the image-processing section 22 can generate medical images that selectively display a desired object from the image data.

Furthermore, if the image data are accompanied with information indicating a diseased area, then the image-processing section 22 specifies, on the basis of this information, the position and size of a diseased area in the generated medical images. The image-processing section 22 makes information that indicates the specified position and size of a diseased area accompany the generated medical images.

By the way, conditions for the image-processing section 22 to generate medical images may be stored in the image-processing section 22 in advance, or information that indicates conditions assigned by the operator may be received from the operation unit 402. The same can be said of conditions for the above-mentioned threshold processing.

The image-processing section 22 outputs the generated medical images to the display controller 30. The display controller 30 causes the display unit 401 to display the medical images. By the way, if the image data is accompanied with information that indicates the position and size of a diseased area, then the display controller 30 specifies the part that corresponds to the diseased area in the medical images based on this information, and the display controller 30 may cause the part to be displayed differently from the others. As a specific example, the display controller 30 applies a different color to the specified part, or the display controller 30 may emphasize or highlight the specified part such that the diseased area may be displayed distinguishably in medical images.

In addition, an image storage section 23 may be provided to store medical images so that medical images generated by the image-processing section 22 can be stored in the image storage section 23. With the embodiment in such a configuration, for example, the image-processing section 22 generates medical images for each timing and causes them to be stored in the image storage section 23. The display controller 30 reads out medical images stored in the image storage section 23 and causes the display unit 401 to display the medical images read out in chronological order or in sequence. In this way, it is possible to observably display a targeted body part undergoing chronological changes in a predetermined region (for example, a lung M1) like a motion picture on the display unit 401.

Figure 4:
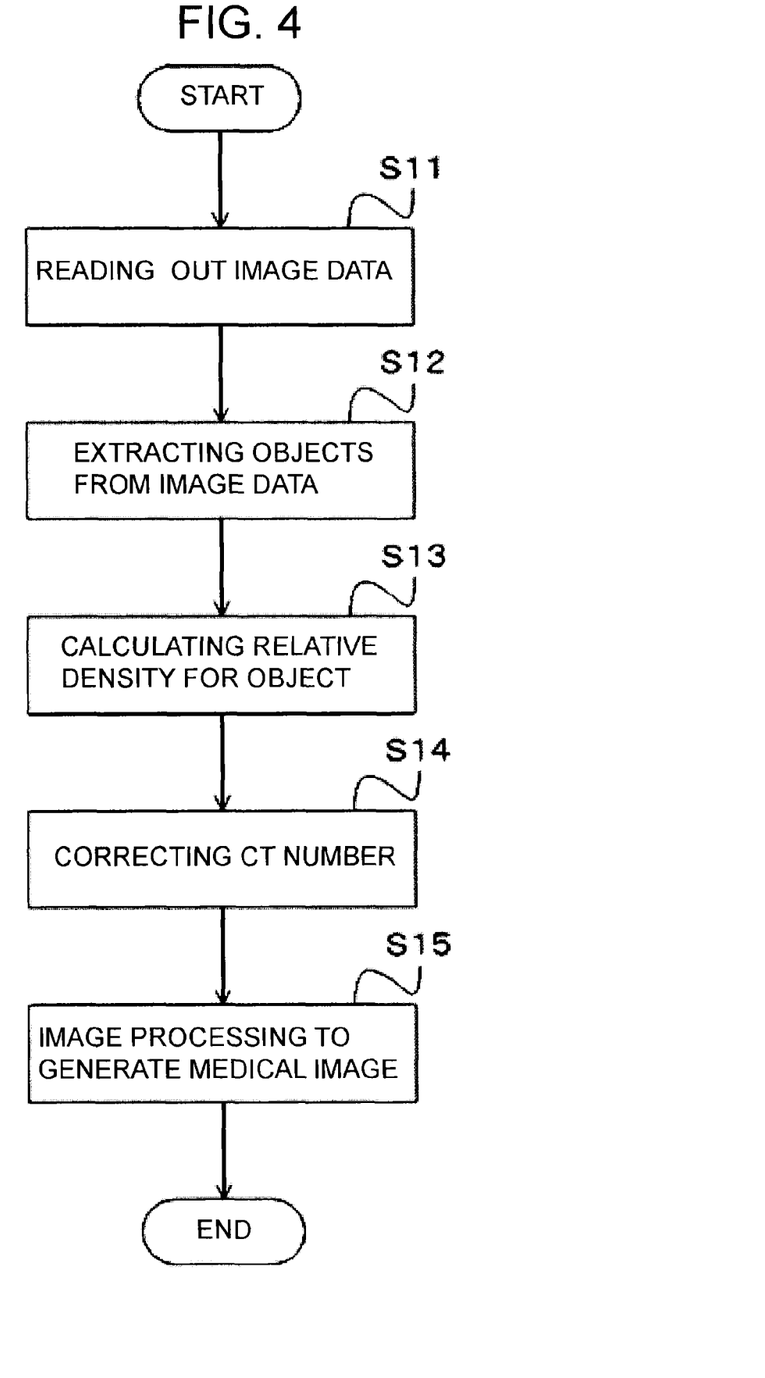
FIG. 4 is a flowchart describing a series of actions taken by the medical image-processing apparatus as an embodiment.

Now, a series of actions taken by the medical image-processing apparatus as this embodiment are described with reference to FIG. 4, which is a flowchart showing a series of actions taken by the medical image-processing apparatus.

(Step S11)

The analysis section 21 at first reads out, from the image data storage unit 10, a plurality of sets of image data that have been acquired by scanning a subject at different timings, set by set of image data for respective acquisition timings. The analysis section 21 outputs the respective sets of image data, which have been read out, to the object-extraction part 211, and the analysis section 21 instructs the object-extraction part 211 to extract objects.

(Step S12)

The object-extraction part 211, upon receiving the image data for each of the timings, extracts objects from a region such as the lungs or the heart from the respective sets of image data, based on voxel values in each set of medical image data. The object-extraction part 211, after extracting an object in each region, executes processing based on biological information, for example, segmentation processing. As a result, the object-extraction part 211 specifies, as object to be analyzed for each timing, an object that corresponds to a region (for example, a lung) that is predetermined as substantially identical throughout the images acquired at different timings. The object-extraction part 211 makes each piece of information indicating the object that has been specified for a corresponding timing accompany the image data from which the information has been extracted. The object-extraction part 211 outputs the image data with this information to the correction part 212.

(Step S13)

The correction part 212 receives the image data for each timing from the object-extraction part 211. The correction part 212 extracts the information that indicates an object from each set of image data.

The correction part 212 calculates the volume of the object that indicates, for example, a region to be analyzed, based on the information indicating the extracted object. On the assumption that the mass of the extracted object is constant all through (for example, at a sample value), the correction part 212 divides the mass by the volume, and thereby the correction part 212 calculates a relative density for the object. In this way, the relative density of the object, which is the analyzed object in the image data, is calculated for each set of image data.

(Step S14)

In addition, the correction part 212 has, in memory beforehand, management information that indicates changes in CT numbers in relation to changes in relative density. FIG. 3 shows an example of such management information. In FIG. 3, while the vertical axis expresses relative densities, the horizontal axis expresses CT numbers. This management information is prepared in advance on the basis of the result of, for example, an experiment in which relations between relative densities and CT numbers are measured. The management information prepared is stored in the correction part 212.

The correction part 212 compares the relative density of the object calculated for each set of image data with the management information, which is shown in FIG. 3, and thereby specifies the divergence of CT numbers that has occurred in connection to chronological density-changes of the region. Specifically, the correction part 212 calculates the differences of the relative densities of the object that correspond to different timings, from the relative density of the object that corresponds to a predetermined timing, set as a reference. The correction part 212 specifies the divergence in CT numbers that corresponds to the difference in relative densities on the basis of the management information. By the way, in the above-mentioned description, the relative density of the object that corresponds to a predetermined timing is assumed as reference for specifying the divergence in CT numbers. The present embodiment is, however, not restricted to this. For example, a relative density as a predetermined sample value may be employed as reference for specifying the divergence in CT numbers.

The correction part 212 corrects CT numbers for the part that corresponds to the object being analyzed in the image data, based on the information that indicates the specified divergence in CT numbers, so that CT numbers for an anatomically identical area correspond one another throughout the plurality of sets of image data. With the operation controlled in this way, in a case where a divergence in CT numbers occurs between sets of image data due to density changes caused by chronological expansion and contraction or shape-alteration, the medical image-processing apparatus is capable of recognizing, by such processing as mentioned above, anatomically identical areas as areas having the same CT numbers (i.e., areas having the same composition).

(Step S15)

The correction part 212 outputs the image data whose CT numbers have been corrected to the image-processing section 22. As a result, for example, when positional matching by specifying an anatomically identical position is executed through a plurality of sets of image data acquired at different timings, the image-processing section 22 can specify anatomically identical areas as the area with the same CT numbers. The medical image-processing apparatus can improve the precision of positional matching by applying such positional matching as this method together with positional matching in accordance with another method (for example, positional matching based on morphological features). Furthermore, since the divergence in CT numbers has been corrected, the image-processing section 22 can achieve similar results from the processing of the respective sets of image data even in a case where medical images are generated to selectively display a desired object by performing threshold processing on CT numbers.

The image-processing section 22 receives image data that have been acquired at different timings and whose CT numbers have been corrected, from the correction part 212 or from the diseased-part-specifying part 213. At this instant, the image-processing section 22, for example, specifies anatomically identical areas throughout the respective sets of image data on the basis of CT numbers in each set of image data, and thereby, the image-processing section 22 may correlate them. In other words, the image-processing section 22 may utilize corrected CT numbers of image data for improving the precision of positional matching performed on the respective sets of image data.

In addition, the image-processing section 22 may perform threshold processing on the CT numbers of the image data. By performing such threshold processing, it is possible to generate medical images that selectively display a desired object on the basis of the image data.

By the way, the image-processing section 22 may be made to store in memory in advance, conditions that are to be applied for the image-processing section 22 to generate medical images, or it may be configured to receive information that indicates conditions assigned by the operator from the operation unit 402. The same is said of the conditions applied to the above-mentioned threshold processing.

The image-processing section 22 outputs generated medical images to the display controller 30. The display controller 30 makes the display unit 401 display the medical images.

By the way, the above-mentioned description is an example of correcting CT numbers based on relative densities. However, embodiments are not restricted to this. For example, calculation may be made of the degree of the chronological shape-alteration of a region targeted for analysis, and CT numbers can be corrected based on this information. Also, the correction part 212 may correct CT numbers based on volume changes of the object. In this case, information that indicates changes in CT numbers in relation to volume changes is stored as management information in the correction part 212. The correction part 212 specifies the divergence in CT numbers by referring the calculated volume of the object to the management information, and then the correction part 212 corrects the divergence.

Figure 5:
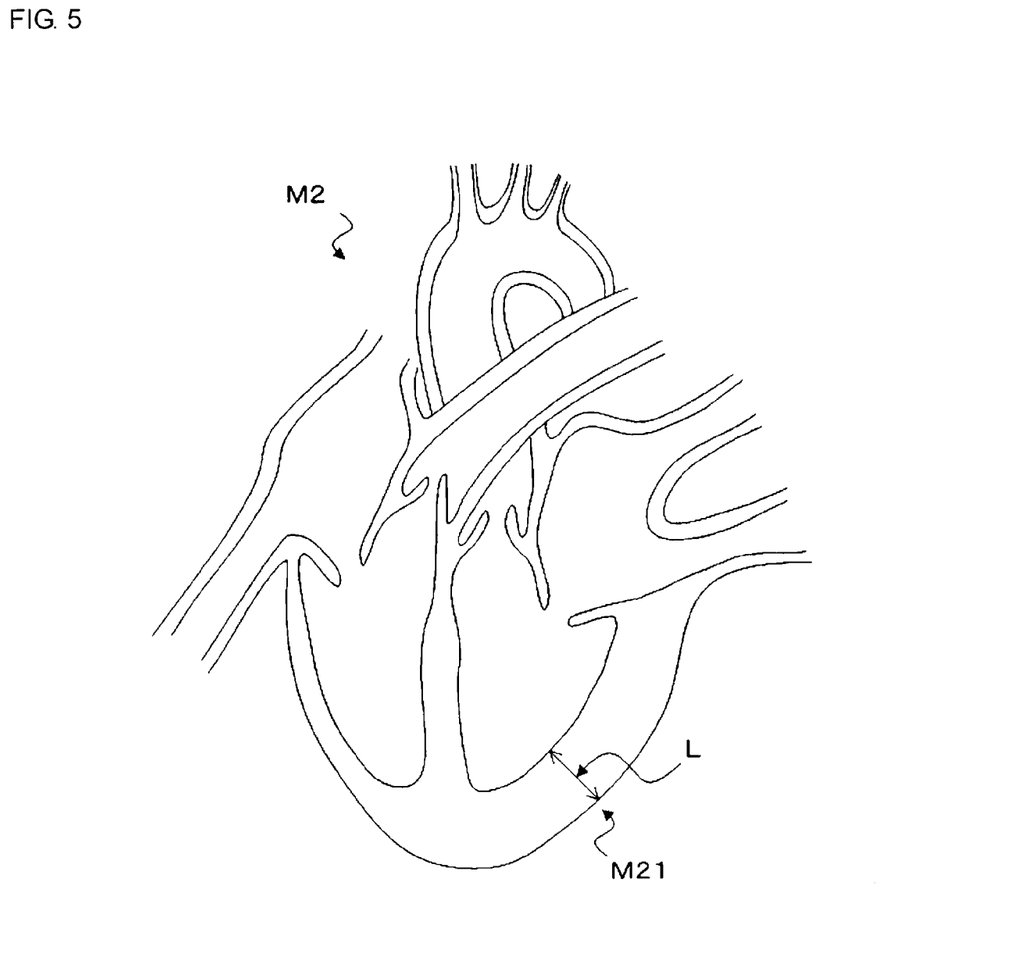
FIG. 5 is a drawing for explaining an embodiment that is applied for the heart.

Furthermore, in a case where the width of an area, for example, the myocardium, (i.e., the thickness of the myocardium) periodically changes within a certain range in synchronization with the beating of the heart, CT numbers may be corrected on the basis of width changes of such an area. For example, FIG. 5 shows such an embodiment applied to the heart. Reference numeral "M2" in FIG. 5 indicates the heart while "M21" indicates the myocardium near the left ventricle. In this case, information that indicates changes in CT numbers in relation to changes in the thickness L of the myocardium M21 is stored as management information in the correction part 212 in advance. The correction part 212 calculates the thickness L of the myocardium M21 as an object of the heart M2. The correction part 212 specifies the divergence in CT numbers by referring the calculated thickness L to the management information and corrects the divergence. Furthermore, instead of the width of a predetermined area, the divergence in CT numbers may be specified based on the surface area of a predetermined area. In such a way, any size information that indicates the dimension of a region changing in motion may be employed including any of the above-mentioned width, area, and volume. In addition, this size information may be calculated for the entirety of the object under observation or may be calculated only for a particular part.

As explained above, the medical image-processing apparatus as the present embodiment is capable of recognizing anatomically identical areas as areas having the same CT numbers (i.e., areas having the same composition) by such processing as described above, even in a case where a divergence in CT numbers occurs between sets of image data due to density changes caused by chronological expansion and contraction or shape-alteration. As a result, for example, when positional matching by specifying an anatomically identical region is executed through a plurality of sets of image data that have been acquired by scanning a subject at different timings, the image-processing section 22 can specify the region as the area having the same CT numbers.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

DESCRIPTION OF NUMBERED PARTS

Numeral 10 designates an image data storage unit; 20, image-processing unit; 21, analysis section; 211, object-extraction part; 212, correction part; 213, diseased-part-specifying part; 22, image-processing section; 23, image storage section; 30, display controller; 40, U/I; 401, display unit; 402, operation unit; and 500, X-ray scanning unit.

What is claimed is:

1. A medical image-processing apparatus, comprising:
    an image data memory configured to store respective sets of image data that have been acquired by scanning a targeted diseased region undergoing chronological shape-alteration in a subject, the scanning having been executed at predetermined respective timings; and
    processing circuitry configured to
        extract image data of the targeted diseased region out of each of the respective sets of image data,
        calculate respective degrees of shape-alteration of the targeted diseased region in the respective extracted sets of image data, wherein the respective degrees of shape-alteration are surface areas of a predetermined area of the targeted diseased region, and
        correct CT numbers of the respective sets of image data that have been extracted for the targeted diseased region, based on the respective calculated degrees.

2. The medical image-processing apparatus according to claim 1, wherein the processing circuitry executes correction such that CT numbers for areas having a same composition in the targeted diseased region are matched throughout the respective sets of image data.

3. The medical image-processing apparatus according to claim 2, wherein the processing circuitry is further configured to
    specify areas in the targeted diseased region having matched CT numbers throughout the respective sets of image data after the correction, as areas having the same composition, and
    generate medical images, respectively, by executing predetermined image-processing on the respective sets of image data.

4. The medical image-processing apparatus according to claim 2, further comprising an interface configured to specify, based on CT numbers, an area that indicates the targeted diseased region in image data among the respective sets of image data after the correction.

5. The medical image-processing apparatus according to claim 1, wherein the processing circuitry corrects the CT numbers based on the calculated surface areas and management information, wherein the management information is stored in a memory and indicates changes in CT numbers in relation to changes in the surface area of the targeted diseased region.

6. An X-ray CT apparatus, comprising:
    a medical scanner configured to acquire a plurality of sets of image data by scanning a targeted diseased region undergoing chronological shape-alteration in a subject, the scanning being executed at predetermined respective timings; and
    processing circuitry configured to
        extract image data of the targeted diseased region out of each of the respective sets of image data,
        calculate respective degrees of shape-alteration of the targeted diseased region in the respective extracted sets of image data, wherein the respective degrees of shape-alteration are surface areas of a predetermined area of the targeted diseased region, and
        correct CT numbers of the respective sets of image data that have been extracted for the targeted diseased region, based on the respective calculated degrees.

7. A medical image-processing method performed by a medical image-processing apparatus, the method comprising:
    acquiring a plurality of sets of image data from an image data memory, which is configured to store respective sets of image data that have been acquired by scanning a targeted diseased region undergoing chronological shape-alteration in a subject, the scanning having been executed at predetermined respective timings;
    extracting image data of the targeted diseased region out of each of the respective sets of image data;
    calculating respective degrees of shape-alteration of the targeted diseased region captured in the respective extracted sets of image data, wherein the respective degrees of shape-alteration are surface areas of a predetermined area of the targeted diseased region; and
    correcting CT numbers of the respective sets of image data extracted for the targeted diseased region, based on the respective calculated degrees.

* * * * *